(12) United States Patent
Hainard

(10) Patent No.: US 9,107,711 B2
(45) Date of Patent: Aug. 18, 2015

(54) SCREW THREAD WITH FLATTENED PEAKS

(71) Applicant: Stryker Trauma SA, Selzach (CH)

(72) Inventor: Nicolas Hainard, Fontainemelon (CH)

(73) Assignee: Stryker Trauma SA (CH)

( * ) Notice: Subject to any disclaimer, the term of this patent is extended or adjusted under 35 U.S.C. 154(b) by 57 days.

(21) Appl. No.: 13/771,677

(22) Filed: Feb. 20, 2013

(65) Prior Publication Data

US 2014/0236245 A1    Aug. 21, 2014

(51) Int. Cl.
*A61B 17/04* (2006.01)
*A61B 17/86* (2006.01)
*A61F 2/08* (2006.01)
*A61B 17/80* (2006.01)

(52) U.S. Cl.
CPC ......... *A61B 17/8057* (2013.01); *A61B 17/8605* (2013.01)

(58) Field of Classification Search
CPC .... A61B 17/84; A61B 17/842; A61B 17/844; A61B 17/864; A61B 17/8625; A61B 17/8685
USPC ........... 606/300–321, 286, 291; 411/399, 411
See application file for complete search history.

(56) References Cited

U.S. PATENT DOCUMENTS

| | | | |
|---|---|---|---|
| 1,876,796 A * | 9/1932 | Trbojevich | 411/423 |
| 3,388,935 A | 6/1968 | Hjalsten | |
| 4,040,756 A | 8/1977 | Donegan | |
| 4,332,502 A * | 6/1982 | Wormald et al. | 403/343 |
| 5,722,808 A * | 3/1998 | Pritchard | 411/366.3 |
| 6,821,278 B2 * | 11/2004 | Frigg et al. | 606/291 |
| 7,179,260 B2 | 2/2007 | Gerlach et al. | |
| 7,997,842 B2 | 8/2011 | Diekmeyer | |
| 2005/0261688 A1 | 11/2005 | Grady et al. | |
| 2005/0277937 A1 | 12/2005 | Leung et al. | |
| 2007/0276386 A1 | 11/2007 | Gerlach et al. | |
| 2009/0118773 A1* | 5/2009 | James et al. | 606/308 |
| 2011/0218580 A1* | 9/2011 | Schwager et al. | 606/308 |

FOREIGN PATENT DOCUMENTS

EP    0230678 A1    8/1987
EP    2364657 A1    9/2011

* cited by examiner

*Primary Examiner* — Matthew Lawson
*Assistant Examiner* — Si Ming Lee
(74) *Attorney, Agent, or Firm* — Lerner, David, Littenberg, Krumholz & Mentlik, LLP

(57) ABSTRACT

A bone fastener for use in orthopedic surgery for fixing an implant to bone has a threaded or unthreaded shaft configured to engage bone and a head having a thread on an outer surface to engage the implant. The thread on the head of the fastener has a profile in cross section that includes arcuate peaks with a flat on the outer surface of the peak.

18 Claims, 9 Drawing Sheets

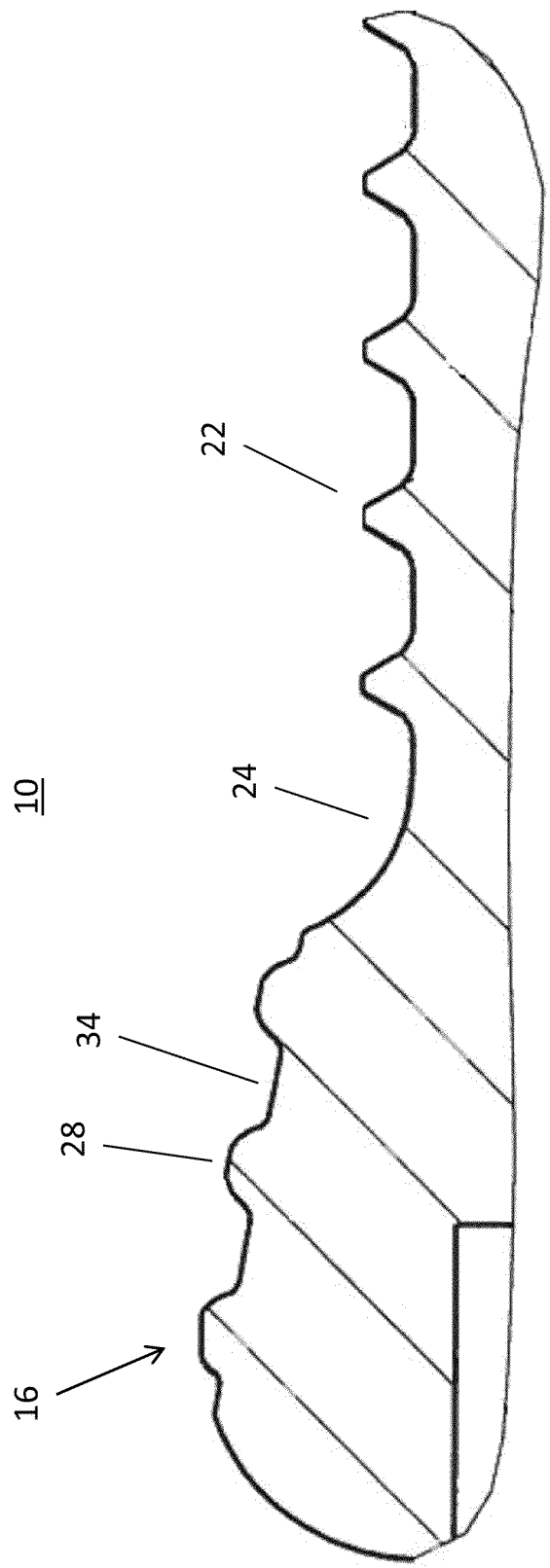

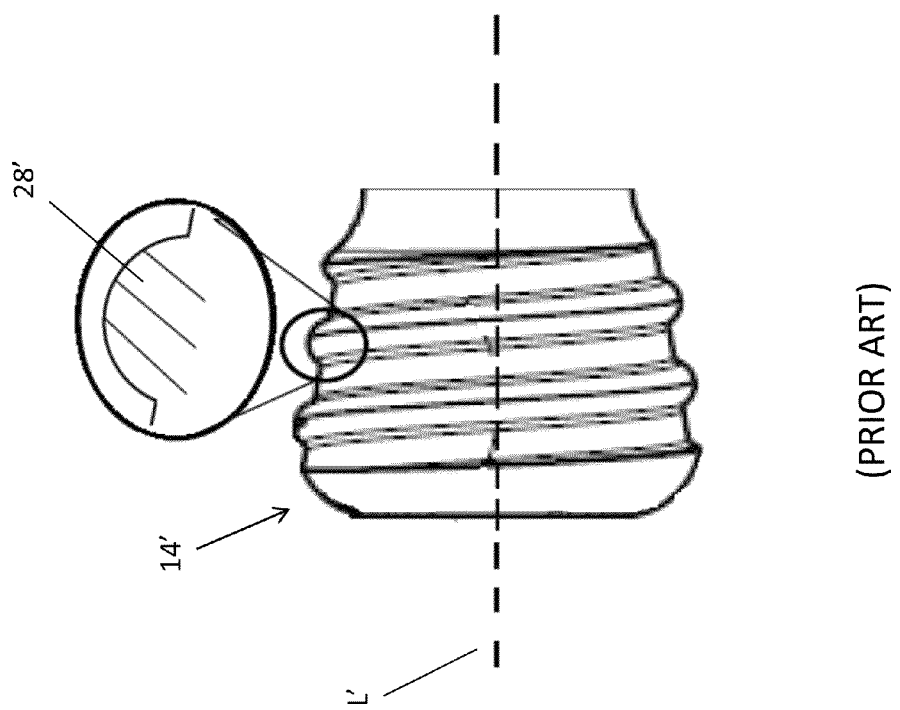

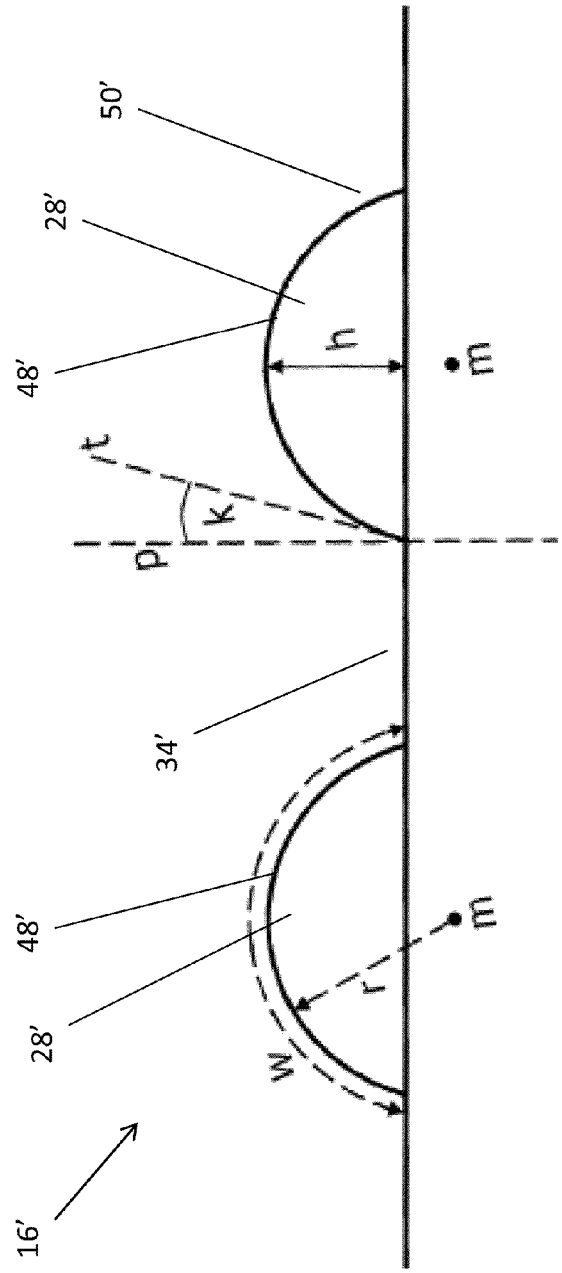

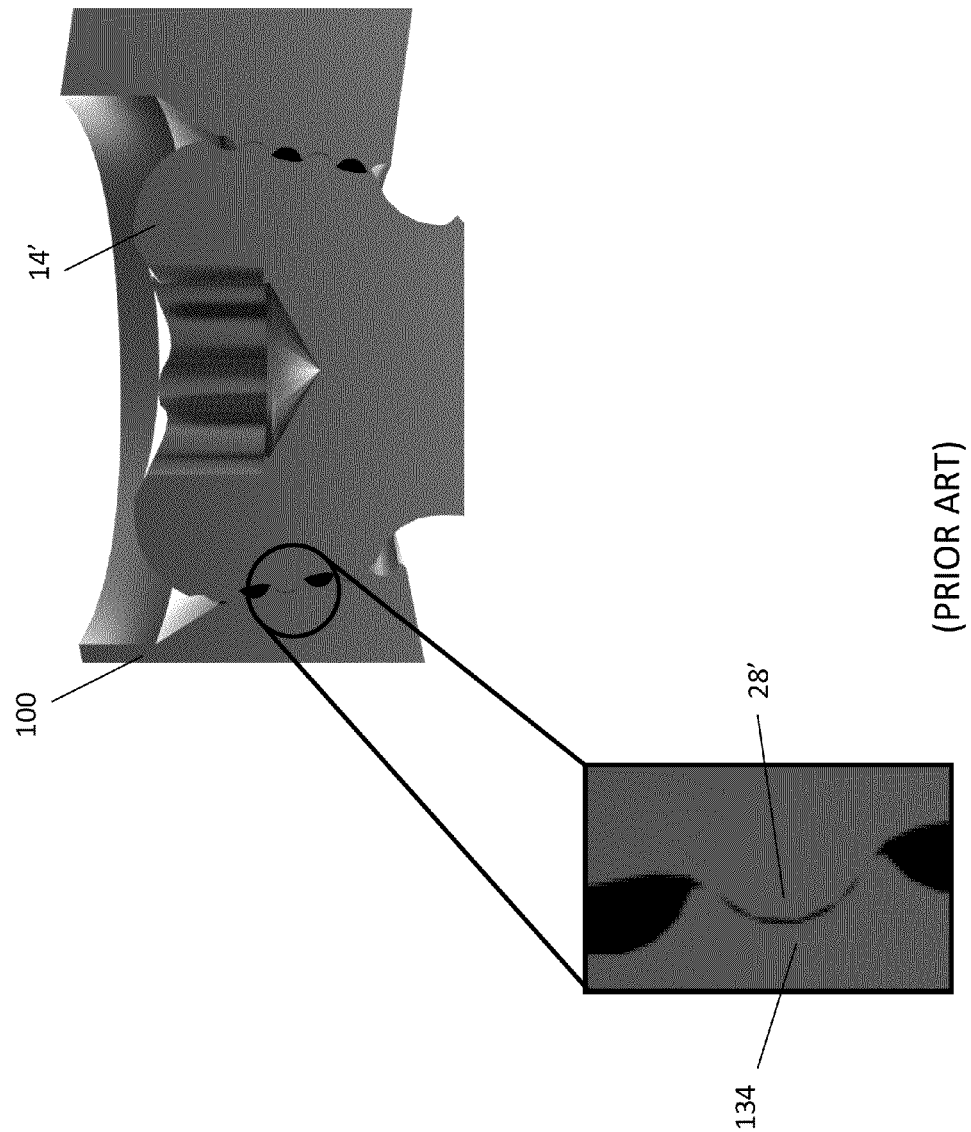

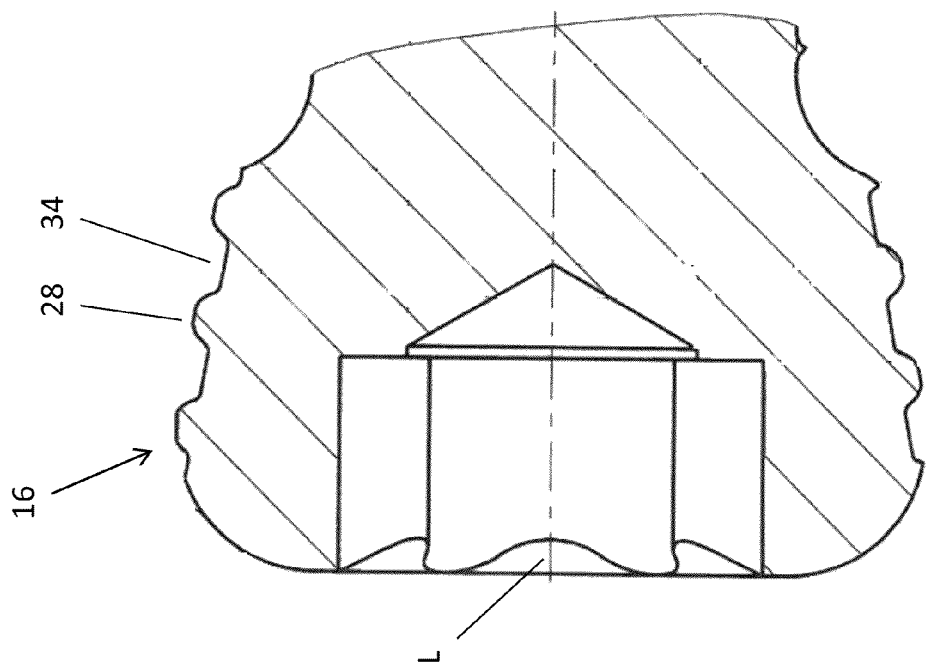

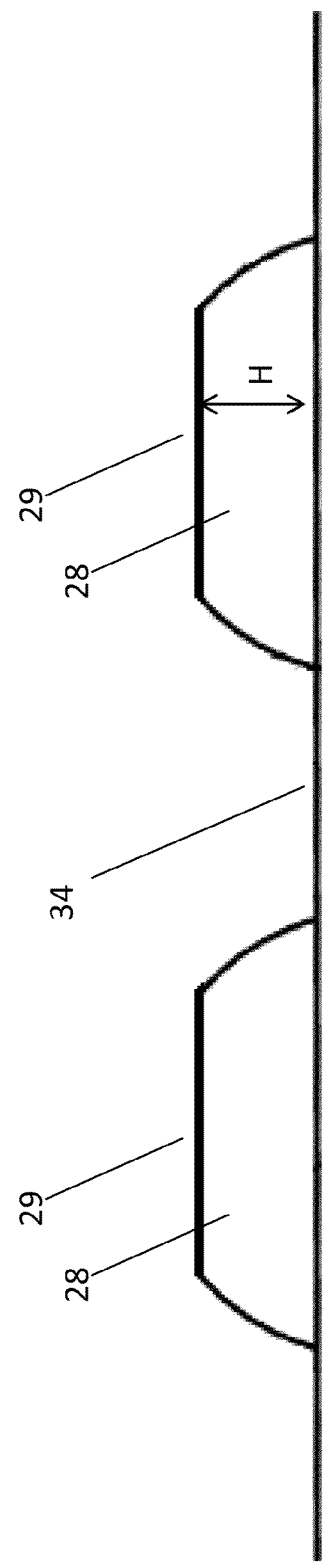

SCREW THREAD WITH FLATTENED PEAKS

FIELD OF THE INVENTION

The present disclosure generally relates to a bone fastener such as a bone screw or bone peg for use in orthopedic surgery, preferably for fixing an implant such as a bone plate to bone.

BACKGROUND OF THE INVENTION

Bone screws are available in a plurality of variations for different applications. Bone screws which can be secured to a bone plate or a similar implant are also known as locking screws. For locking the bone screw to the bone plate, a head of the bone screw is provided with a thread that mates with a corresponding thread on an inner surface of a plate hole.

U.S. Patent Publication Nos. 2005/0277937 and 2009/0192550 relate to a typical locking screw which is intended to be secured to a bone plate. The head of the bone screw has a spherical shape and a thread with V-shaped ridges. The thread of the head is a double lead thread which mates with an internal thread of a plate hole. The ridges of the thread provided in the plate hole have a defined angle relative to the plate, whereby the bone screw is correspondingly fixed to the bone plate at a predetermined angle.

The threaded head of a locking screw may also have a cylindrical or conical shape. U.S. Pat. No. 7,179,260 and U.S. Patent Publication No. 2007/0276386 relate to a bone plate system comprising a locking screw with such a head. The screw head is completely or partially threaded to be received in a threaded plate hole. U.S. Patent Publication No. 2005/0261688 relates to a further bone screw having a conically-tapered and threaded head. The flanks and peaks of the threaded head have a trapezoidal shape for mating with internal threads of a plate hole.

EP 0 230 678 A1 relates to an endosteal screw implant used in dentistry comprising a shaft and a conical head with a spherically shaped portion. The shaft of the screw has a thread which is cylindrically shaped and rounded on its external edges for fixing the shaft into a jaw bone.

The conventional bone fasteners for locking applications have several drawbacks. During the screwing-in operation of the bone fastener head into the implant, the thread of a head of the fastener can tilt and jam within the threaded portion of the implant hole. Thereby, the flanks and peaks of the threaded head and the threaded hole may get damaged. Moreover, splinters from the bone drilling as well as other materials like parts of human tissue can contaminate the edges and grooves of the threads, whereby the thread of the threaded head and the internal thread of the hole of the implant can jam.

BRIEF SUMMARY OF THE INVENTION

In one embodiment, a bone fastener for use in orthopedic surgery for fixing an implant to bone includes a shaft and a head. The shaft has a first core diameter and a first thread projecting outwardly from the first core diameter. The head is formed on the shaft and is tapered at an angle towards the shaft. The taper of the head forms a plurality of second core diameters each larger than the first core diameter of the shaft. The head has a second thread projecting outwardly from at least a portion of the plurality of second core diameters. The second thread is formed to engage the implant. The bone fastener includes a central longitudinal axis through the shaft and the head, and the second thread has a profile in cross section including a plurality of peaks. The plurality of peaks has a flat portion intermediate two curved portions.

The profile of the second thread may include a plurality of valleys, each of the plurality of valleys being planar. The plurality of valleys may form a longitudinal axis, and the plurality of peaks may also form a longitudinal axis. The longitudinal axis of the plurality of peaks may be parallel or non-parallel to the longitudinal axis of the plurality of valleys. The longitudinal axis of the plurality of peaks and the longitudinal axis of the plurality of valleys may each be non-parallel to the central longitudinal axis of the bone fastener. The two curved portions of one of the plurality of peaks may connect two of the plurality of valleys to one of the plurality of peaks.

In another embodiment, an implant system for use in orthopedic surgery for fixation of bone includes a bone plate and at least one bone fastener. The bone plate has an upper surface, a lower surface and at least one hole extending through the bone plate upper surface and lower surface. The at least one hole has a threaded portion. The at least one bone fastener includes a shaft and a head. The shaft has a first core diameter and a first thread projecting outwardly from the first core diameter. The shaft is configured to engage bone. A head is formed on the shaft and is tapered at an angle towards the shaft. The taper of the head forms a plurality of second core diameters each larger than the first core diameter of the shaft. The head has a second thread projecting outwardly from at least a portion of the plurality of second core diameters. The second thread is formed to engage the threaded portion of the at least one hole of the bone plate. The bone fastener may include a central longitudinal axis through the shaft and the head. The second thread has a profile in cross section including a plurality of peaks, the plurality of peaks having a flat portion intermediate two curved portions.

The profile of the second thread may include a plurality of valleys, each of the valleys being planar. The plurality of valleys may form a longitudinal axis and the plurality of peaks may form a longitudinal axis. The longitudinal axis of the plurality of peaks may be parallel or non-parallel to the longitudinal axis of the plurality of valleys. The longitudinal axis of the plurality of peaks and the longitudinal axis of the plurality of valleys may each be non-parallel to the central longitudinal axis of the bone fastener. The two curved portions of one of the plurality of peaks may connect two of the plurality of valleys to one of the plurality of peaks.

BRIEF DESCRIPTION OF THE DRAWINGS

These and other features, aspects and advantages of the present disclosure will become apparent form the following detailed description take in conjunction with the accompanying drawings, wherein:

FIG. 1B is a sectional view of the bone fastener of FIG. 1A;

FIG. 2 is a side view of the head of a bone fastener according to the prior art with an enlarged sectional view of a thread peak;

FIG. 3 is a sectional view of peaks of the thread of the bone fastener head shown in FIG. 2;

FIG. 4 is a sectional view of the bone fastener head shown in FIG. 2 inserted in a hole of a bone plate, with an enlarged sectional view of the engagement of the bone fastener in the hole of the bone plate;

FIG. 5 is a sectional view of the head of the bone fastener illustrated in FIG. 1A;

FIG. 7 is a sectional view of peaks of the thread of the bone fastener head shown in FIG. 1A.

DETAILED DESCRIPTION

Figure 1A:
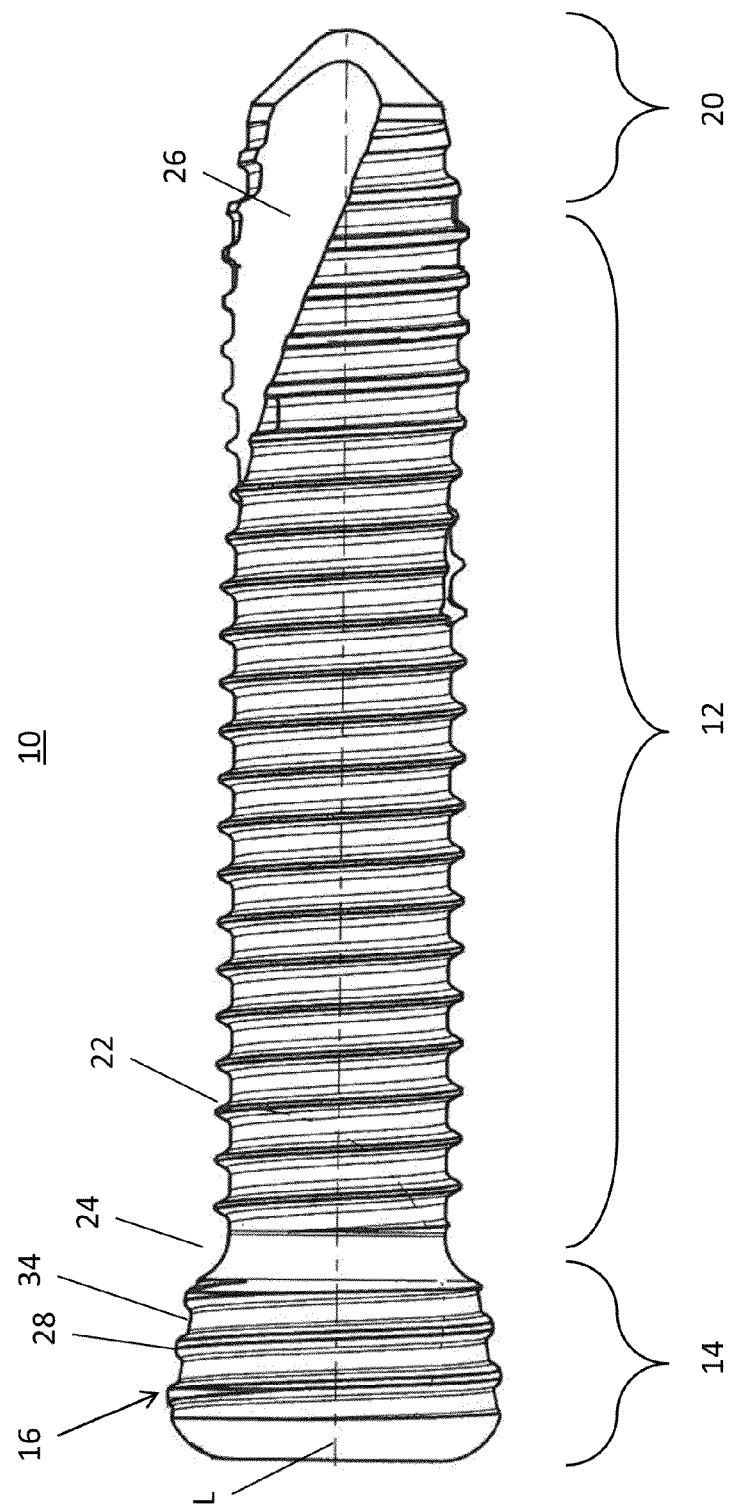
FIG. 1A is a side view of a bone fastener.

Referring to FIGS. 1A-B, there are shown side view and sectional views of one embodiment of a bone fastener according to an aspect of the invention. The bone fastener is in the form of a bone screw 10 for use as a locking screw in orthopedic surgery for fixing an implant (shown in FIGS. 4, 8) to bone. The bone screw 10 includes a shaft 12 configured to engage bone and a head 14 having a thread 16 on an outer surface to engage the implant. The bone screw 10 has a longitudinal axis L. The head 14 is provided at a distal side of the shaft 12 and a tip 20 is provided at a proximal side of the shaft 12. The tip 20 may be formed as a cone having an opening angle of, for example, 60° to 120°.

Further, as illustrated in FIGS. 1A-B, the shaft has a threaded portion 22. Trapezoidally shaped peaks of the threaded portion 22 are separated by valleys having a planar profile in cross section. The threaded portion 22 of the shaft may have a constant thread pitch. The threaded portion 22 extends from the tip 20 to a non-threaded portion 24 adjacent to the head end of the shaft 12.

The thread of the threaded portion 22 of the shaft 12 may be formed as a conventional self-tapping thread, wherein two helically winding cutting grooves 26 are provided at the proximal end of the shaft 12 near the tip 20 for feeding material away. In this cutting area, the shaft 12 may have a greater core diameter. However, the outer diameter of the thread of the threaded portion 22 may be constant along the whole length of threaded portion 22 in the axial direction of the bone screw 10. Thereby, the force during screwing in the bone screw 10 into bone is reduced.

As shown in FIGS. 1A-B, the head 14 of bone screw 10 is adjacent to the non-threaded portion 24 of shaft 12, and the core diameter of the head 14 if constant or a plurality of core diameters if tapered are each greater than the core diameter of the shaft 12. Further, the core of the screw head 14 may have a generally conical shape and an outer diameter of the thread 16 of the head 14 may gradually taper inward toward the non-threaded portion 24 of bone screw 10. The thread 16 may be a single-lead thread or a multiple thread in the form of a double thread (i.e., a double-lead thread). The thread 16 of the head 14 illustrated in FIGS. 1A-B is a single-lead thread with peaks 28 of the thread 16 being separated from each other by valleys 34. As can be seen in FIGS. 1A-B, the thread of the bone screw head 14 can extend along the entire length of the head in the axial direction of the screw.

FIG. 2 illustrates a screw head 14' according to the prior art. In this embodiment, the screw head 14' includes a single-lead threading 16' with peaks 28' separated by valleys 34' having a planar profile in cross section. The threading 16' is illustrated in more detail in FIG. 3. Each curved peak 28' forms an arc segment 48'. The arc segment can be a segment of a circle, of an ellipse, or of any other curved structure.

The arc segment 48' is defined by a radius of curvature r and a center point m. The radius of curvature r of the arc segment 48' may be, for example, between approximately 0.05 mm and 3.0 mm, in particular between 0.1 mm and 1.0 mm. Moreover, each arc segment 48' has an angular range w which may be, for example, between 30° and 200°, in particular between 45° and 180°.

As illustrated in FIG. 3, the arc segment 48' is not semicircular (i.e. w<180°) and the peak 28' of the arc segment 48' is defined by an angle k between a plane p including the core diameter of the thread 16' of the screw head 14' and a tangent t to the arc segment 48' where it intersects the core. This angle k can be between −10° and 90°, in particular between 0° and 50°. Further, the more strongly inclined portion 50' of the arc segment 48' can be defined by curved flanks 50'. Each curved flank 50' connects the valley 34' with the top of peak 28'. It should be noted that the flanks 50' may generally have a different curvature than the arc segments 48' defining the peaks 28'.

Moreover, as shown in FIG. 3, each curved peak 28' can be defined by a height h which extends from a plane defined by the core of the screw head 14' to the top of peak 28'. This height h of the peak 28' can be between 0.1 mm and 3.0 mm, in particular between 0.15 mm and 1.5 mm.

FIG. 4 illustrates the screw head 14' inserted into a bone plate 100 within an internally double-threaded hole of the bone plate. As can be seen in FIG. 4, particularly in the enlarged view, the peak 28' makes near full contact with a valley 134 of the bone hole threading. This high degree of contact area between the threading in the bone screw and the bone hole may increase the potential for fretting while the bone plate is implanted in a patient. The increased contact area and fretting may result in an increase in the amount of torque required to remove the bone screw during extraction of the bone plate. For example, the bone screw described above may only require approximately 4 Nm of torque during insertion of the bone screw, while 10 Nm or more of torque may be required during extraction of the bone screw. It would be preferable for the required insertion torque to be approximately the same as the required extraction torque. One feature that may have an influence on the amount of extraction torque required for a bone screw is shape of the thread.

FIG. 5 illustrates the head 14 of the bone screw 10 described above in FIGS. 1A-1B. Similar to the prior art bone screw described with reference to FIGS. 2-4, the bone screw 10 illustrated in FIG. 5 includes a head with threading 16, including peaks 28 and valleys 34. However, as illustrated in FIGS. 6-7, the peaks 28 are not fully arcuate, but rather have a flat 29.

Figure 6A:
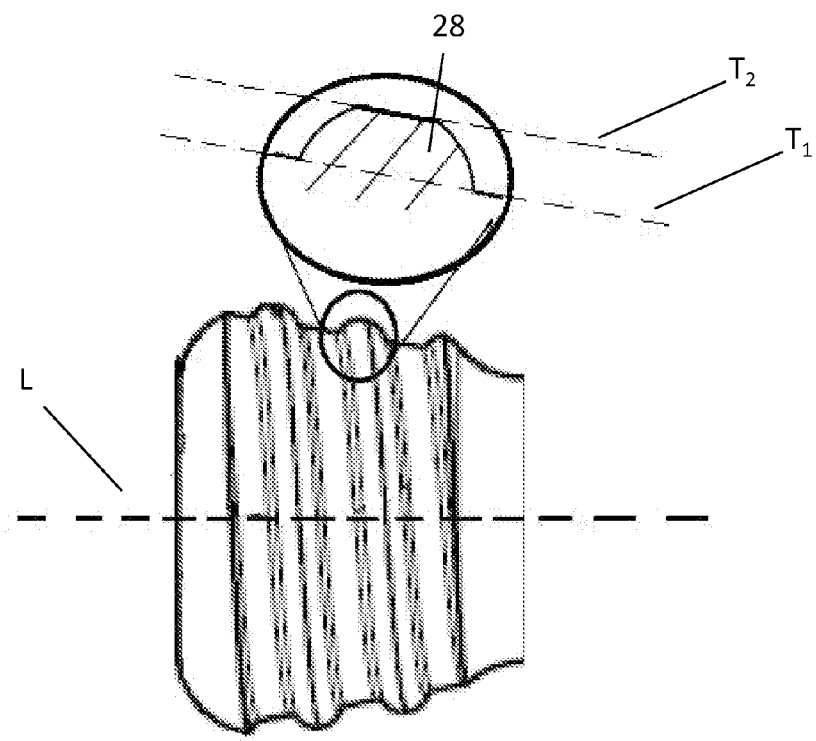
FIG. 6A is a side view of the head of the bone fastener illustrated in FIG. 1A with an enlarged sectional view of a thread peak, with FIG. 6B showing a side view of an alternate embodiment of the bone fastener of FIG. 6A.
Figure 6B:
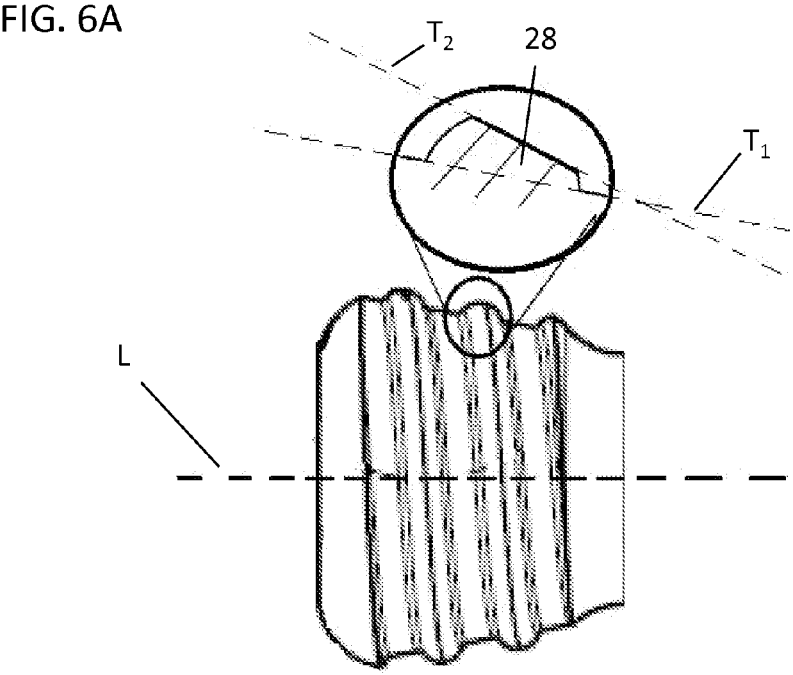

In one embodiment as shown in FIG. 6A, the flat 29 of peak 28 has a taper $T_2$ substantially parallel to the taper $T_1$ of the core of the head 14. The taper $T_2$ of the flat 29 may alternately be non-parallel to the taper $T_1$ of the core of the head 14 as shown in FIG. 6B. For example, the taper $T_2$ of the flat 29 may be greater or less than the taper $T_1$ of the core of the head 14. In one example, the taper $T_2$ of the flat 29 may be parallel to the longitudinal axis L of the bone screw 10. In other examples, the taper $T_2$ of the flat 29 may be non-parallel to the longitudinal axis L of the bone screw 10. Similarly, the flat 29 may have a height H above the core of the head 14. The value of the height H may be varied while still falling within the scope of the invention. The valleys 34 may be substantially planar between the peaks 28.

The inclusion of the flat 29 reduces the contact surfaces between the thread 16 of the head 14 and the corresponding internal thread of a hole in a bone plate 100. This, in turn, minimizes the risk of potential fretting. Fretting is known to cause a higher required extraction torque when removing bone screws 10 during explantation of a bone plate 100. The addition of flats 29 to the peaks 28 of threading 16 in the head 14 of the bone screw 10 may reduce the required extraction torque by 50%, for example.

Figure 8:
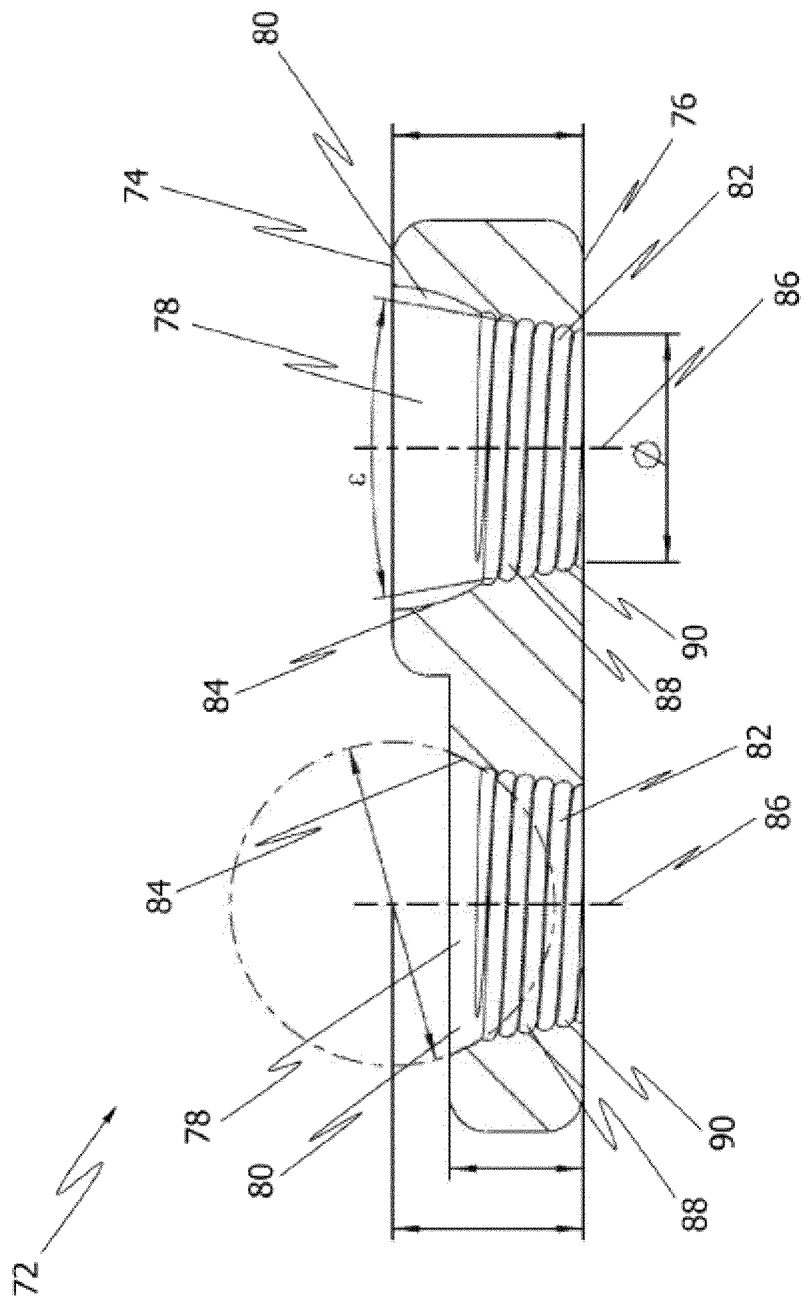
FIG. 8 is a cross-sectional view of an alternate embodiment of a bone plate.

FIG. 8 illustrates in a cross-sectional view an embodiment of an implant in the form of a bone plate 72 that can be adapted as needed (e.g., in terms of shape, thickness, etc.) for use in orthopedic surgery for fixation of bone. The bone plate 72 has an upper surface 74 and a lower surface 76. Further, as shown in FIG. 8, the bone plate 72 includes at least two holes 78 extending through the upper surface 74 and the lower surface 76 for receiving a bone fastener (e. g., a bone screw as described above and shown in FIG. 1A). The bone plate 72 may have a varying thickness along its entire length.

Each hole may 78 include an optional upper portion 80 and a lower threaded portion 82 configured to mate with the thread of the head of the bone fastener. The upper portion 80 of each hole 78 may have an inward taper 84 generally having a conical or curved (e.g., spherical) shape. The curved or spherical shape of the inward taper 84 of the upper portion 80 can be defined by an segment of a circle or ellipse in cross section with a center point arranged on a position along a central axis 86 of the hole 78.

The lower portion 82 of each hole 78 may taper toward the lower surface 76 of the bone plate 72. The taper of the threaded portion 82 is defined by a cone angle $\epsilon$ which may be between 1° and 179°, in particular between 10° and 120°, and more particularly approximately 20° in the embodiment illustrated in FIG. 8. As shown in FIG. 8, the lower threaded portion 82 may include a thread 88 with curved valleys 90 which are provided immediately adjacent to each other. Alternately, the threading of the bone plate 72 may be similar to the threading of bone plate 100 illustrated in FIG. 4. Further, the thread 88 of hole 78 may be a multiple thread (a double thread). In one implementation, an implant system comprises at least the bone plate 72 with the double thread 88 as well as a bone fastening element comprising a head with a single thread (such as the bone screw of FIG. 1A).

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims. Similarly, certain aspects of the disclosure may be combined with other aspects of the disclosure in any reasonable way without diverting from the scope of the invention.

The invention claimed is:

1. A bone fastener for use in orthopedic surgery for fixing an implant to bone, comprising:
    a shaft having a first core diameter and a first thread projecting outwardly from the first core diameter,
    a head formed on the shaft, the head being tapered at an angle towards the shaft, the taper of the head forming a plurality of second core diameters each larger than the first core diameter of the shaft, the head having a second thread projecting outwardly from at least a portion of the plurality of second core diameters, the second thread being formed to engage the implant,
    wherein the bone fastener includes a central longitudinal axis through the shaft and the head,
    wherein the second thread has a profile in cross section including a plurality of peaks, the plurality of peaks having a flat portion intermediate two curved portions,
    wherein the profile of the second thread includes a plurality of valleys, each of the plurality of valleys being planar,
    wherein the second thread includes a transition region between the flat portion of one of the plurality of peaks and an adjacent one of the plurality of valleys, an entire length of the transition region having a convex curvature, and
    wherein the two curved portions are defined by respective arc segments of a circle with a single center point located within the plurality of second core diameters.

2. The bone fastener of claim 1, wherein a longitudinal axis is formed by the plurality of valleys.

3. The bone fastener of claim 2, wherein a longitudinal axis is formed by the plurality of peaks.

4. The bone fastener of claim 3, wherein the longitudinal axis of the plurality of peaks is non-parallel to the longitudinal axis of the plurality of valleys.

5. The bone fastener of claim 3, wherein the longitudinal axis of the plurality of peaks is parallel to the longitudinal axis of the plurality of valleys.

6. The bone fastener of claim 3, wherein the longitudinal axis of the plurality of peaks is non-parallel to the central longitudinal axis of the bone fastener.

7. The bone fastener of claim 3, wherein the longitudinal axis of the plurality of valleys is non-parallel to the central longitudinal axis of the bone fastener.

8. The bone fastener of claim 1, wherein the two curved portions of one of the plurality of peaks connect two of the plurality of valleys to one of the plurality of peaks.

9. The bone fastener of claim 1, wherein an oblique angle is formed about a point at which the transition region meets the adjacent one of the plurality of valleys.

10. An implant system for use in orthopedic surgery for fixation of bone, comprising:
    a bone plate having an upper surface and a lower surface;
    at least one hole extending through the bone plate upper surface and lower surface, the at least one hole having a threaded portion;
    at least one bone fastener comprising a shaft having a first core diameter and a first thread projecting outwardly from the first core diameter, the shaft configured to engage bone and a head formed on the shaft, the head being tapered at an angle towards the shaft, the taper of the head forming a plurality of second core diameters each larger than the first core diameter of the shaft, the head having a second thread projecting outwardly from at least a portion of the plurality of second core diameters, the second thread being formed to engage the threaded portion of the at least one hole of the bone plate,
    wherein the bone fastener includes a central longitudinal axis through the shaft and the head,
    wherein the second thread has a profile in cross section including a plurality of peaks, the plurality of peaks having a flat portion intermediate two continuously curved portions,
    wherein the profile of the second thread includes a plurality of valleys, each of the plurality of valleys being planar,
    wherein the second thread includes a transition region between the flat portion of one of the plurality of peaks and an adjacent one of the plurality of valleys, an entire length of the transition region having a convex curvature, and
    wherein the two continuously curved portions are defined by respective arc segments of a circle with a center point located within the plurality of second core diameters.

11. The implant system of claim 10, wherein a longitudinal axis is formed by the plurality of valleys.

12. The implant system of claim 11, wherein a longitudinal axis is formed by the plurality of peaks.

13. The implant system of claim 12, wherein the longitudinal axis of the plurality of peaks is non-parallel to the longitudinal axis of the plurality of valleys.

14. The implant system of claim 12, wherein the longitudinal axis of the plurality of peaks is parallel to the longitudinal axis of the plurality of valleys.

15. The implant system of claim 12, wherein the longitudinal axis of the plurality of peaks is non-parallel to the central longitudinal axis of the bone fastener.

16. The implant system of claim 12, wherein the longitudinal axis of the plurality of valleys is non-parallel to the central longitudinal axis of the bone fastener.

17. The implant system of claim 10, wherein the two curved portions of one of the plurality of peaks connect two of the plurality of valleys to one of the plurality of peaks.

18. The implant system of claim 10, wherein an oblique angle is formed about a point at which the transition region meets the adjacent one of the plurality of valleys.

* * * * *